United States Patent
Hepp

(10) Patent No.: US 9,354,211 B2
(45) Date of Patent: May 31, 2016

(54) METHOD OF TESTING A WELD BETWEEN TWO PLASTIC PARTS

(75) Inventor: Franz Hepp, Metzingen (DE)

(73) Assignee: BIELOMATIK LEUZE GMBH&CO.KG, Nuffen (DE)

( * ) Notice: Subject to any disclaimer, the term of this patent is extended or adjusted under 35 U.S.C. 154(b) by 324 days.

(21) Appl. No.: 13/880,921

(22) PCT Filed: Dec. 21, 2011

(86) PCT No.: PCT/EP2011/073658
§ 371 (c)(1),
(2), (4) Date: Jul. 1, 2013

(87) PCT Pub. No.: WO2012/085131
PCT Pub. Date: Jun. 28, 2012

(65) Prior Publication Data
US 2013/0269438 A1    Oct. 17, 2013

(30) Foreign Application Priority Data

Dec. 21, 2010    (DE) .................. 10 2010 055 294

(51) Int. Cl.
| | |
|---|---|
| *G01N 33/00* | (2006.01) |
| *B29C 65/02* | (2006.01) |
| *B29C 65/82* | (2006.01) |
| *B29C 65/00* | (2006.01) |
| *G01N 21/84* | (2006.01) |
| *G01N 29/04* | (2006.01) |
| *B29C 65/16* | (2006.01) |

(52) U.S. Cl.
CPC .............. *G01N 33/00* (2013.01); *B29C 65/02* (2013.01); *B29C 65/16* (2013.01); *B29C 65/1635* (2013.01); *B29C 65/8253* (2013.01); *B29C 65/8292* (2013.01); *B29C 66/954* (2013.01); *G01N 21/84* (2013.01); *G01N 29/04* (2013.01)

(58) Field of Classification Search
CPC    B29C 65/02; B29C 65/8253; B29C 65/8292; B29C 66/954; G01N 21/84; G01N 29/04
USPC .......................................................... 73/788
See application file for complete search history.

(56) References Cited

U.S. PATENT DOCUMENTS

| | | | | |
|---|---|---|---|---|
| 6,643,002 | B2 * | 11/2003 | Drake, Jr. ............... | G01N 29/04 356/72 |
| 7,244,482 | B2 * | 7/2007 | Bager ..................... | A61F 5/445 428/35.2 |
| 7,938,007 | B2 * | 5/2011 | Huebler ................. | G01N 29/07 73/622 |

(Continued)

FOREIGN PATENT DOCUMENTS

| | | |
|---|---|---|
| DE | 102005000002 A | 7/2006 |
| JP | 11147258 A * | 6/1999 |

(Continued)

*Primary Examiner* — Freddie Kirkland, III
(74) *Attorney, Agent, or Firm* — Andrew Wilford

(57) ABSTRACT

The invention relates to a method for determining whether two plastics components (1, 2) to be welded to each other in a joint plane are welded to each other after a welding process has been carried out, characterized in that the position of a reference plane is determined from a reference point before the welding process is carried out, then the welding process is carried out, and the position of the joint plane or the thickness of the components (1, 2) welded to each other is determined from the reference point during or after the welding process.

8 Claims, 1 Drawing Sheet

(56) References Cited

U.S. PATENT DOCUMENTS

| | | | | |
|---|---|---|---|---|
| 8,104,347 B2 * | 1/2012 | Den Boer | ............... | G01N 29/07 73/596 |
| 8,778,120 B2 * | 7/2014 | Kreischer | ........... | A61M 39/146 156/272.8 |
| 8,812,251 B2 * | 8/2014 | Ihn | ..................... | G01N 27/026 702/182 |
| 2002/0048015 A1 * | 4/2002 | Drake, Jr. | ............... | G01N 29/04 356/72 |
| 2004/0089640 A1 * | 5/2004 | Bager | .................. | A61F 5/445 219/121.64 |
| 2005/0000641 A1 * | 1/2005 | Hartmann | .............. | B23K 26/18 156/272.8 |
| 2012/0265449 A1 * | 10/2012 | Ihn | ....................... | G01N 27/026 702/33 |
| 2015/0053005 A1 * | 2/2015 | Smith | .................... | G01N 29/04 73/579 |

FOREIGN PATENT DOCUMENTS

| | | | | |
|---|---|---|---|---|
| JP | 11172258 B | 6/1999 | | |
| JP | 2004001071 A | * | 1/2004 | ............ B23K 26/18 |
| JP | 2004001071 B | 1/2004 | | |

* cited by examiner

METHOD OF TESTING A WELD BETWEEN TWO PLASTIC PARTS

CROSS REFERENCE TO RELATED APPLICATIONS

This application is the US-national stage of PCT application PCT/EP2011/073658 filed 21 Dec. 2011 and claiming the priority of German patent application 102010055294.1 itself filed 21 Dec. 2010.

FIELD OF THE INVENTION

The invention relates to a method of determining whether two plastics parts to be welded to each other in a joint plane are welded to each other after a welding process has been carried out.

BACKGROUND OF THE INVENTION

The foundation for the invention is the laser transmission welding method, which is known per se, in which two parts consisting of a plastic material are brought into contact in the region of a joint plane. Subsequently, a welding process is performed by a laser beam that melts the interfaces of the parts in the region of the joint plane, and a permanent bond of the two parts with one another is thus produced after cooling. For this purpose, it is necessary for one part to be transparent to the laser and the other part to be opaque or absorbent to the laser beam.

Depending on the application of the finished overall part, which consists at least of the two plastics parts to be welded to one another, high strength or also safety demands are placed on the final product. Therefore, it is necessary not only to execute the welding process to join together the two plastics parts, but rather to monitor quality as or after the welding process is carried out.

For ensuring quality in such a manner, DE 10 2005 000 002 A1 proposes a method of detecting thermal damage during laser transmission welding and a corresponding device for carrying out this method. Using this known method, during the laser transmission welding of plastics, the possible occurrence of burns on the beam entry side of one plastics part can be detected accompanying the process. For this purpose, the radiation originating from the burn is detected by a corresponding element (sensor), and to therefore allow discarding of a damaged part in the context of mass production of such parts.

However, this known method has the disadvantage of an elaborate and therefore complex construction, so that it is not suitable or is only suitable to a limited extent for mass production and in particular ensuring the quality of plastics parts produced by mass production.

OBJECT OF THE INVENTION

The invention is therefore based on the object of improving a method of the above-described type for determining whether or not two plastics parts to be welded to each other in a joint plane are welded to each other after a welding process has been carried out, with respect to the detection precision and the reaction time.

SUMMARY OF THE INVENTION

According to the invention before the welding process is carried out, the location of a reference plane is ascertained from a reference point, subsequently the welding process is carried out, and during or after the ending of the welding process, the location of the joint plane or the thickness of the parts welded to one another is ascertained from the reference point. Before the welding of two parts, one having the thickness d1 and one having the thickness d2, an interface always exists between these two parts that is the joint surface of the part faces directed toward one another, and the two parts are to be permanently bonded to one another in the region of the joint surface by the laser transmission welding method. This interface is designated hereafter as the joint plane. Before welding, this plane is characterized in that the face of the two parts facing toward one another press against one another nearly completely or with only a negligible gap. According to the invention the location of a reference plane is ascertained proceeding from a reference point. This reference plane can be the joint plane between the two faces of the parts facing toward one another. However, in this case it can also be the surface of one or the other part that is on the side facing away from the joint plane. This surface can also be designated as a free surface, because it is accessible. Subsequently, the welding process is carried out, and the surfaces of the two parts facing toward one another heat up, melt, and fuse together in the region of the joint plane, so that a clearly delimited joint plane does not result therefrom, but rather a joint region arises. This joint region cannot be definitely delimited with respect to its structure from the original material of the two parts, so that a flowing transition arises from the original material before the welding process is carried out and the joint region (after the welding process is carried out). This joint region is also designated as the weld seam penetration. Furthermore, according to the invention, the location of the joint plane (more precisely the joint region) or the thickness of the two parts welded to one another is ascertained from the reference point during or after the ending of the welding process. This is because after welding, the joint plane fuses, which has the result that the measured thickness Dn of the part changes. This change results from the value of the two individual thicknesses of the parts that are designated as d1 and d2. Before the joining process, the thickness was Dv=d1+d2. After the welding process is carried out (possibly also even as the welding process is carried out), the total thickness Dn can be obtained from one of the two individual thicknesses d1 or d2 in consideration of the weld seam penetration s. The ascertained value for the location of the joint plane or the joint region after the welding process is carried out or the ascertainment of the thickness of the two parts that are welded to one another is, within predefinable tolerances, a measure of whether the two plastics parts to be welded to one another in the joint plane are welded to one another as intended after the welding process is carried out or whether a flaw has occurred. Depending on which measure was ascertained for the location of the joint plane after the welding process was carried out or which thickness of the parts welded to one another was ascertained, information can be derived therefrom as to whether there is a flaw (for example, a shrinkage hole) in one of the two plastics parts (for example, because of an injection molding flaw) or a flaw in the weld seam (as a result an interface that is not bonded or is only partially bonded).

As a result, rapid measuring and, resulting therefrom, short measuring times are possible using the method according to the invention that can be executed as and/or after the welding process is carried out. Because of the precision in the determination of the reference plane, the joint plane, and the thickness of the parts welded to one another, each proceeding from the reference point, a very precise determination is possible as to whether the welding process for connecting the two plastics parts to one another was carried out correctly or whether it was a faulty process.

In order to allow the rapid measuring times, in a refinement of the invention the ascertainment of the location of the joint plane and the thickness of the parts welded to one another is performed by a laser beam measurement. Alternatively, an ultrasonic measurement can also be performed for this purpose. Furthermore, it is alternatively provided that the ascertainment of the location of the joint plane is performed before the welding process is carried out by an ultrasonic measurement and the ascertainment of the thickness of the parts welded to one another is performed during or after the welding process by a laser beam measurement (or vice versa). Various measurement possibilities are thus proposed that also require different devices (for example, laser beam source, ultrasound source, corresponding sensors, and the like), and these devices can be optimally adapted to the materials used of the plastics parts and the geometry thereof.

BRIEF DESCRIPTION OF THE DRAWING

The invention is described in greater detail hereafter for further explanation, for which reference is made to FIGS. 1 and 2 that are schematic views illustrating the invention.

SPECIFIC DESCRIPTION OF THE INVENTION

Figure 1:
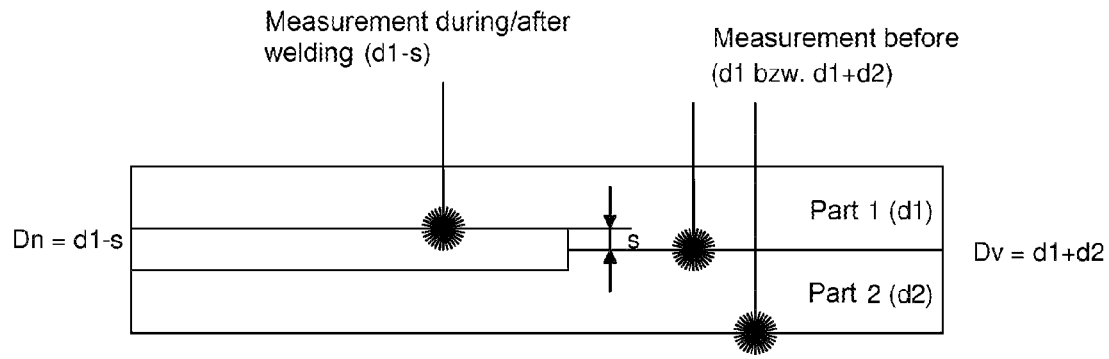

FIG. 1 shows as an embodiment a laser beam measurement, wherein proceeding from a reference point (for example, the location of the laser beam source), the thickness d1 of the part 1 and the thickness d2 of the part 2 are determined, i.e., the surface of the part 1 facing away from the laser beam source is a first reference plane and the surface of the part 2 facing away from the laser beam source is a further reference plane that are ascertained before the welding process. Subsequently, the welding process is carried out and the two parts 1 and 2 are welded to one another at the joint plane. As a result of the welding, the clearly delimited joint plane disappears and becomes a joint region. This joint region is also ascertained relative to the reference point as Dn−s in consideration of the weld seam thickness s. Alternatively or additionally thereto, the resulting total thickness Dn of the entire part (consisting of the joined parts 1 and 2) can also be ascertained. This resulting total thickness Dn is typically somewhat less as a result of the joining process than the sum of the original individual thicknesses d1 and d2 of the two parts 1 and 2. As a result, the difference between the sum Dv of the individual thicknesses d1 and d2 before the welding process and the total thickness Dn resulting after the welding process is a measure of a properly carried out welding process or a faulty welding process.

Figure 2:
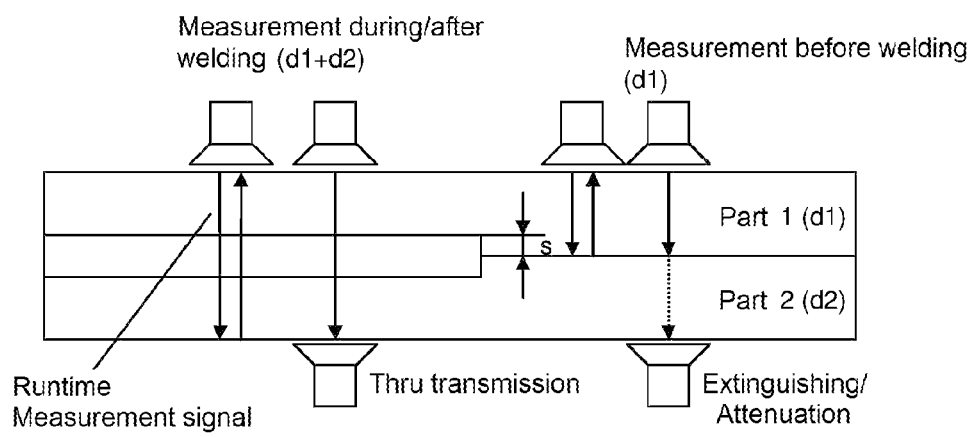

Alternatively to the laser distance measurement, an ultrasonic distance measurement is provided in FIG. 2. The same statements as already made on the laser distance measurement according to FIG. 1 also apply here. First, before the welding process is carried out, an ultrasonic distance measurement is carried out using corresponding means to ascertain the individual thicknesses d1 and d2 of the two parts 1 and 2. This is performed either in that ultrasound is directed into one part, reflected back from the second part, and directed out again, and the runtime is determined as a measure of the thickness d1 of the part 1. The total thickness Dv before the welding process can be ascertained, for example, in that an ultrasonic signal is fed into the surface of the first part 1, passes through both parts 1 and 2, and emerges from or is reflected back by the outer surface of the second part 2. The runtime for the ultrasonic signal through the two parts is also a measure of the thickness of the two parts 1 and 2 before the welding process here. This is also true for the thickness measurement after the welding process is carried out. A runtime measurement or alternatively through transmission can also be performed here. This is shown in FIG. 2 in the left half by the section of the two parts 1 and 2. A measure can also be obtained here, from the ascertained total thickness D before the welding process (FIG. 2, right half) and the new total thickness D resulting after the welding process is carried out (upon observation of FIG. 2 on the left side), from which it can be derived whether the welding process, in particular the laser transmission welding, was successfully executed (so that the two plastics parts have been bonded to one another correctly) or whether a flaw has occurred (so that this resulting total part does not meet the requirements and, for example, in the case of mass production, must be discarded therefrom).

The invention will be explained once again in other words hereafter.

Before two part halves 1 and 2 of the thickness d1 and the thickness d2 are welded together, an interface (joint plane) always exists between the two parts.

This interface can be located according to the invention either by
- laser distance measurement (in the case of laser-transparent parts, or in the case of the welding of a radiation-transparent part with a radiation-absorbing part) or by
- ultrasound (in the impulse echo method by measuring the sound runtimes in the plastic).

After the welding, the interface fuses and the measured thickness of the part changes:
- in the case of laser distance measurement of two transparent parts, to the value d1+d2
- in the case of laser distance measurement of one transparent part and one absorbing part to the value d1−s (wherein s=weld seam penetration into the transparent part→the melts mix together and a part of the absorbent material also becomes absorbent; the measured thickness is thus reduced)
- in the case of ultrasonic thickness measurement to d1+d2.

The advantages of the method are:
- rapid measurement, short measuring times
- information about the depth of the flaw makes interpretation possible, as to whether it is a shrinkage hole in the part (injection molding flaw) or a flaw in the weld seam (non-connected interface).

Method variants:
- Laser distance measurement using lasers or E, whose wavelength is such that the plastic is transparent in this wavelength range,
- adaptation of the laser type/wavelength and the result analysis to the optical properties of the employed plastic (absorption, optical penetration depth),
- ultrasonic measurement using touching ultrasonic sensor,
- ultrasonic measurement through the air using noncontacting ultrasonic sensor,
- ultrasonic measurement in the through transmission method.

The invention claimed is:

1. A method of determining whether faces of two plastic parts to be welded to each other at a joint plane are welded to each other after a welding process, one of the parts having a respective thickness and being laser transparent and the other of the parts having a respective thickness and being laser opaque, the method comprising the steps of:

determining before the welding process is carried out, the distance of a reference plane from a reference point, subsequently welding the faces of the parts together to form a weld seam between the parts, and during or after the welding step, determining the distance of the joint plane from the reference point by directing a laser beam through the one laser-transparent part.

2. The method as claimed in claim 1, further comprising after the welding step the step of:

determining a total thickness of the parts welded to one another by laser beam measurement.

3. The method as claimed in claim 1, wherein the distance from the reference plane to the reference point before welding is determined by measuring the thickness of the one plastic part.

4. The method as claimed in claim 1, wherein the distance from the reference plane to the reference point after welding is determined by determining the distance from the reference point to the weld seam.

5. The method as claimed in claim 1, further comprising the step of:

determining a total thickness of the plastic parts welded to one another by ultrasonic runtime measurement whereby ultrasound is reflected after passing through the plastic parts welded to one another, and reflection back through the plastic parts welded to one another.

6. The method as claimed in claim 1, further comprising the step of:

determining a total thickness of the plastic parts welded to one another by ultrasonic through transmission, the plastic parts welded to one another being transmissive to ultrasound.

7. A method of welding a first laser-transparent plastic part of a predetermined first thickness to a second laser-opaque plastic part of a predetermined second thickness, the method comprising the steps of sequentially:

juxtaposing a face of the first part against a face of the second part to define a reference plane;

determining a first distance from a reference point outside the parts through the laser-transparent part to the reference plane between the juxtaposed parts with a laser;

laser-welding the two juxtaposed parts together by directing a laser beam through the first laser-transparent part against the second laser-opaque part at the reference plane to fuse the two faces together at the reference plane;

determining a second distance from the reference point to the weld seam; and comparing the first and second distances to evaluate the weld seam.

8. The method defined in claim 7, further comprising the step of:

prior to welding, determining a first total thickness of the juxtaposed parts;

after welding, determining a second total thickness of the welded-together parts; and comparing the first and second total thicknesses to evaluate the weld seam.

\* \* \* \* \*